United States Patent [19]

Feher

[11] Patent Number: 5,154,608
[45] Date of Patent: Oct. 13, 1992

[54] METHOD AND APPARATUS FOR OCCLUSION ANALYSIS

[76] Inventor: Tibor Feher, Blumenstrasse 9, D-4000 Dusseldorf, Fed. Rep. of Germany

[21] Appl. No.: 709,587

[22] Filed: Jun. 3, 1991

[30] Foreign Application Priority Data

Jun. 12, 1990 [DE] Fed. Rep. of Germany ....... 4018755

[51] Int. Cl.⁵ .............................................. A61C 11/00
[52] U.S. Cl. ......................................... 433/57; 433/55
[58] Field of Search ....................... 433/54, 55, 56, 57, 433/59, 61, 65, 66

[56] References Cited

U.S. PATENT DOCUMENTS 4,034,475  7/1977  Lee ......................................... 433/56
4,305,708 12/1981  Beu ......................................... 433/57

Primary Examiner—Cary E. O'Connor
Attorney, Agent, or Firm—Chilton, Alix & Van Kirk

[57] ABSTRACT

A method and apparatus for determination of the jaw relation and for instrumental occlusion analysis, which permit a reliable diagnosis and treatment for the occlusion. For this purpose, a maxillary model and mandibular model from a patient are fixed in plaster independently of one another and anatomically correctly and are placed one upon the other in an instantaneous occlusal position. For the instantaneous occlusal position, the positioning of the articular cavities of the maxillary model relative to the hinge axis of the mandibular model is determined, and the maxillary model is then displaced three-dimensionally relative to the mandibular model, with symmetrical alignment of the articular cavities relative to the hinge axis. The resulting jaw relation is fixed for an analysis of the malocclusions.

15 Claims, 4 Drawing Sheets

METHOD AND APPARATUS FOR OCCLUSION ANALYSIS

BACKGROUND OF THE INVENTION

1. Field of the Invention

The present invention relates to determining the relationship between the jaws of a patient and particularly to occlusion analysis. More specifically, this invention is directed to apparatus which may be employed for occlusion analysis and especially to such apparatus wherein maxillary and mandibular models derived from a patient may be supported and manipulated relative to one another in order to permit an analysis of malocclusions. Accordingly, the general objects of the present invention are to provide novel and improved methods and apparatus of such character.

2. Description of the Prior Art

It is well known that the functioning of the stomatic system is affected by the teeth, jaw joints, muscles and nerves. It is further known that the spatial position of the mandible and condyles is determined by the cooperating rows of teeth when in the central occlusion position. Functional impairments in the muscle and mandibular joint area are caused by mandibular displacements. Restated, if such a displacement results in the relationship between maxilla and mandible being such that the condyles are not in a balanced, compression-free state in their hinge position, the greatest possible inactivation of the muscle groups exists. This is a condition which may require treatment. A displacement of the mandible frequently occurs upon changes in the occlusion guide paths due to fillings, crowns, interdental spaces, etc. The result of such a displacement may be a loss of the correct physiological position of the mandible and the jaw joints and, consequently, a loss of the physiological central occlusion position. The problem is particularly critical in the case of dorsal/ventral displacements and/or distraction/compression of the jaw joint associated with a unilateral or asymmetrical shift of the condyles. A displaced mandible can be returned into the correct physiological position by means of intervening in the occlusion. However, for such intervention to be successful with minimum patient discomfort, an exact diagnosis of the displacement of the mandible is necessary, i.e., in order to perform the corrective procedure it is necessary to know precisely how the position of the mandible is to be corrected.

Various techniques have been proposed, and in some cases implemented, for performing an occlusion analysis in order to determine the appropriate treatment for correcting a mandible displacement in a patient. One known method consists of articulating the maxilla in relation to the cranium and transferring the mandible by means of a function register. Another known method involves articulating either the mandible or maxilla and, in relation to the articulation, transferring of the opposing jaw by means of a function register.

Exemplary apparatus for performing a typical prior art occlusion analysis may be seen from German Patent No. 2,443,235. This German patent discloses a prior art articulator which includes mandibular and maxillary supports. The mandibular support includes a base plate with a block for the mandibular model and a pair of columns having spherical ends which define a horizontal articulator hinge axis. The maxillary support similarly includes a base plate with a block for the maxillary model. The maxillary support also has an outer arm which receives the spherical ends on the columns of the mandibular support whereby a swivel movement of the two supports relative to one another is permitted. The assembly of the jaw models in such a prior art articulator is usually carried out by first fixing the maxillary or mandibular model, in the form of a plaster cast, into the articulator in relation to the cranium or articulation, i.e., the model is placed in the spatial position relative to the articulator hinge axis which is identical to the hinge axis transferred from the patient. Thereafter, the opposing jaw model, also in the form of a plaster cast, is introduced into the articulator by means of a function register taken from the patient. The articulator allows the movements of the patient's jaws to be simulated and the occlusion to be assessed.

A significant disadvantage of prior art occlusion analysis apparatus and techniques, as briefly described above, resides in the necessity for use of a function register. The use of a function register requires the plotting of the centric relation in the patient and constitutes an important source of error. In general, the manual guiding of the mandible into the centric relation is necessary and is registered as the "instantaneous centric relation" using the centric register. The patient, however, can also be left to adopt the centric relation himself. The instantaneous centric relation can be affected by the defective configuration of the occlusal relief which may be present in the patient in which case a defective muscle reflex action is produced. Such a defective muscle reflex action makes it impossible for the patient to adopt the correct centric relation. Accordingly, the prior art techniques inherently cannot constitute a reliable measure for correct adjustment of the condyles and inaccurate diagnosis become unavoidable.

SUMMARY OF THE INVENTION

The present invention overcomes the above briefly discussed and other deficiencies and disadvantages of the prior art by providing a novel and improved method for the determination of the relationship between the jaws of a patient and for instrumental occlusion analysis. The present invention further encompasses apparatus for use in the practice of this novel method, the method and apparatus allowing a reliable diagnosis and treatment of malocclusion.

In accordance with the invention, a maxillary model and a mandibulary model from a patient are fixed in plaster independently of one another and anatomically correctly. These models are then placed, one upon the other, in an instantaneous occlusal position. In order to ensure that the placement of the models is correct, the positioning of the articular cavities of the maxillary model relative to the hinge axis of the mandibular model is determined. The maxillary model is subsequently displaced relative to the mandibular model, with symmetrical alignment of the articular cavities relative to the hinge axis, and the resulting jaw relation is fixed for an analysis of the malocclusions.

Apparatus for use in the practice of the present invention comprises a mandibular part and a maxillary part, each part having a base plate for supporting a jaw model. The maxillary part is movably mounted on a hinge axis on the mandibular part. The maxillary part has a pair of arms which are positioned on either side of a guide body which supports the base plate. These arms are displaceable independently of one another relative to the guide body.

The method and apparatus of the present invention directly determine the physiological jaw relation as a starting point for the diagnoses and treatment of the occlusion paths. As noted above, models of the maxilla and mandible are made which are independent of one another and anatomically correct. These models are then related to each other, preferably on the basis of the central occlusion position. The apparatus of the invention permits a displacement of the maxillary model with any or all of a sagittal, vertical and horizontal shift. Accordingly, the spatial position of the maxillary model in the occlusal position, preferably in maximum intercuspidation, may be adjusted relative to the instrumental hinge axis. If it is determined that there is a displacement of the maxillary model relative to the hinge axis, the position of the maxillary part can be corrected by unilateral, bilateral or three-dimensional displacement of the movable articular cavities. A symmetrical alignment of the articular cavities makes it possible to establish and fix the physiological jaw relation. The relevant occlusion bite makes the malocclusions obvious.

The present invention allows a simple and precise occlusal analysis and eliminates the need for shaped fossa boxes to simulate side shift and protrusive human jaw movements of a patient. These advantages are produced by the use of a device having upper and lower frames, the frames being aligned in a centric position, which enables the upper frame to pivot on condyles on a hinge axis of the lower frame.

The present invention also allows the asymmetrical caudal/cranial and/or dorsal/ventral displacements of the mandible, which are typical of pathological jaw relations, to be demonstrated with reference to the maxillary model in the instrumental occlusion analysis. Such displacements can be eliminated by correction of the position of the maxillary model. Also, in accordance with the invention, not only is it possible to establish the position of the mandible, and consequently readily determine the interferences occurring between maxilla and mandible, but the invention also permits the malocclusions responsible for the disharmonies to be pinpointed. In this manner, a safe and reliable determination of the jaw relation is possible as a starting point for the treatment of a patient for obtaining the correct positioning of the mandible.

BRIEF DESCRIPTION OF THE DRAWINGS

The present invention may be better understood and its numerous objects and advantages will become apparent to those skilled in the art by reference to the accompanying drawings wherein like reference numerals refer to like elements in the several figures and in which.

DESCRIPTION OF THE DISCLOSED EMBODIMENT

Figure 1:
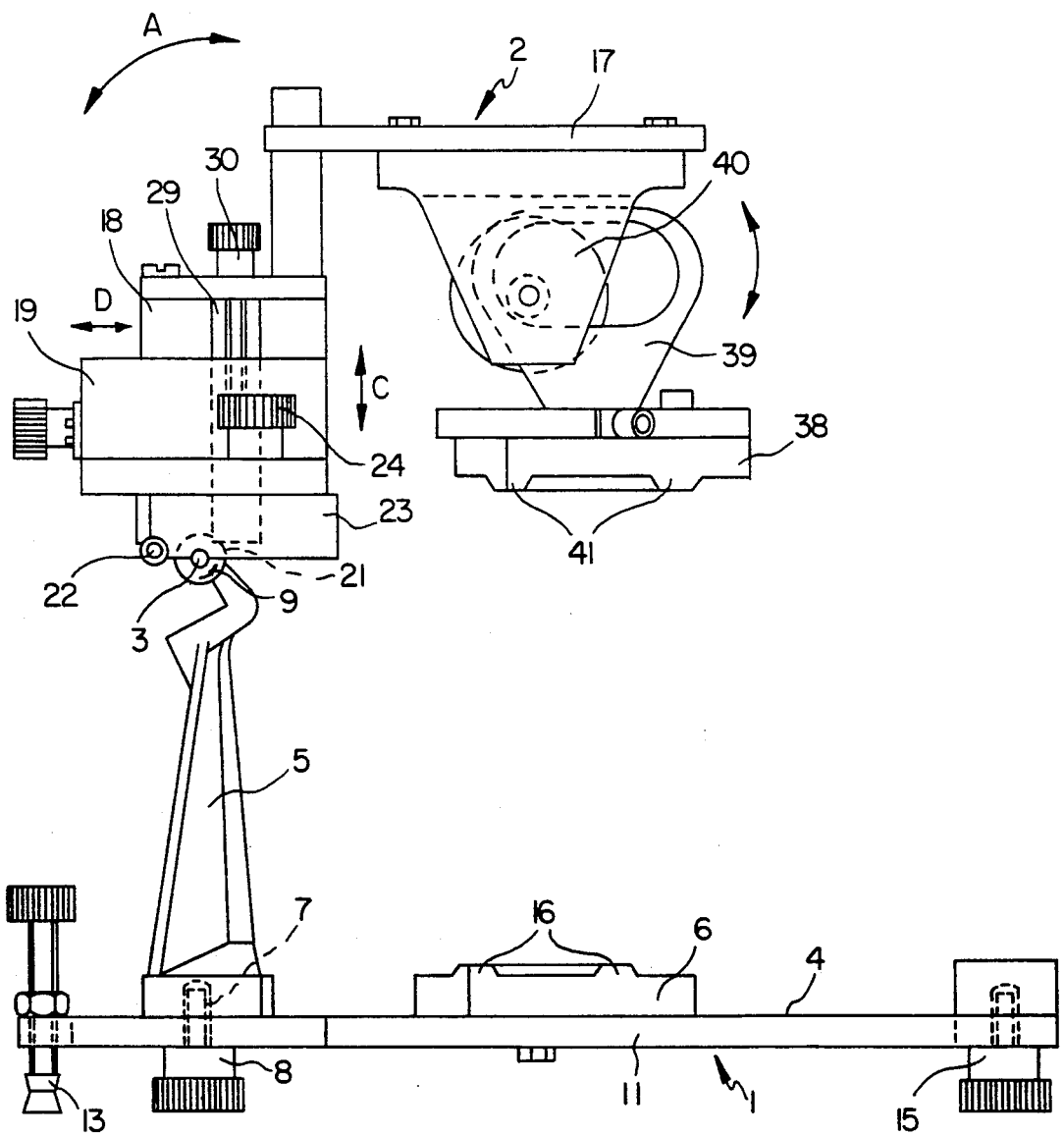
FIG. 1 is a side elevation view of apparatus for use in the practice of the present invention to determine the relationship between the jaws of a patient.

With reference to the drawings, and particularly to FIG. 1, apparatus for occlusion analysis in accordance with the present invention comprises a mandibular part, indicated generally at 1, and a maxillary part, indicated generally at 2. The parts 1 and 2, in the manner to be described below, simulate the human mandible and maxilla. In the apparatus of the present invention, the maxillary part 2 is mounted on the mandibular part 1 so that it can swivel about an axis 3, hereinafter "the hinge axis". The direction of this swivel movement is indicated in FIG. 1 by the double arrow A. This swivel movement is exactly the opposite of the human dentition, in which the mandible moves in relation to the maxilla. However, the relative movement is the same and it has been found preferable to fix the position of the mandibular part 1.

Figure 2:
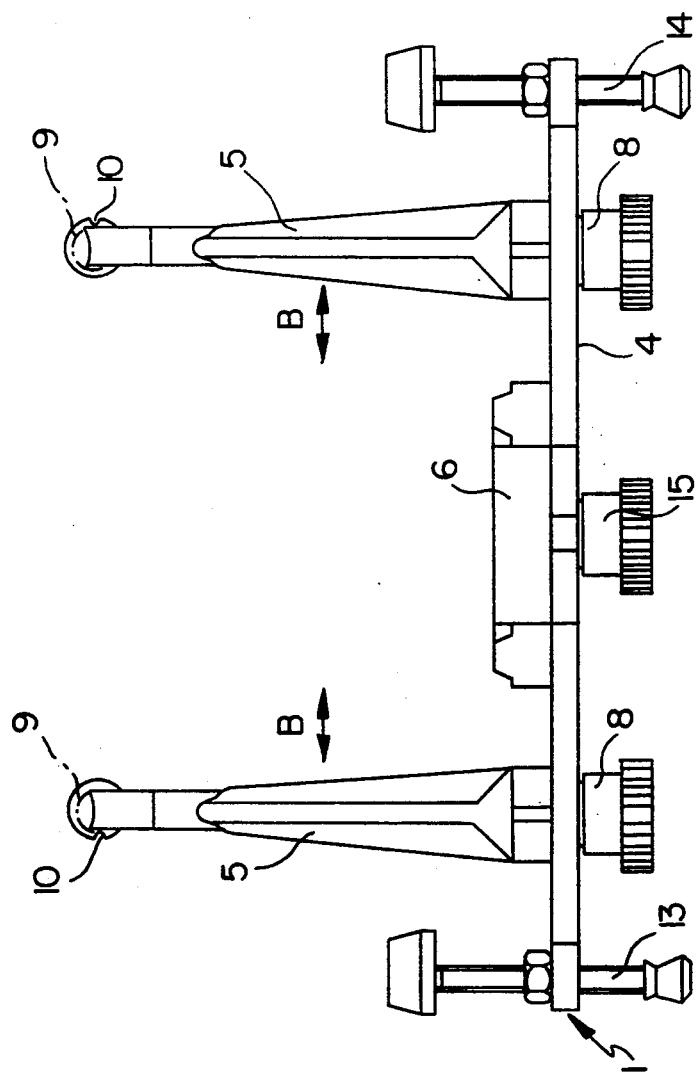
FIG. 2 is a front plan view of the mandibular support of the apparatus of FIG. 1.

Referring jointly to FIGS. 1 and 2, the mandibular part 1 of an occlusion analysis instrument in accordance with the invention comprises a base plate 4. A pair of columns 5, spaced by a distance which may be varied, extend from the base plate 4. A model block 6, the position of which is also adjustable, is further mounted on base plate 4. The columns 5 extend essentially vertically from the base plate 4, i.e., the columns 5 are generally parallelly oriented, and are mutually displaceable in the direction indicated by the double arrows B. In order to permit adjustment of the spacing between the columns 5, a pair of aligned guide slots 7 are provided in the base plate 4. The columns 5 can be locked in a position commensurate with the selected spacing through the use of locking screws 8. Each of the columns 5 is provided, at its free end, with a spherical head 9, these spherical heads defining the articulated or hinge axis 3.

In the manner to be described below, the maxillary part 2 is mounted so that it can execute a swivel movement about the spherical heads 9. Thus, the spherical heads 9 form an instrumental hinge axis and consequently simulate the hinge axis of the mandible. The use of spherical heads ensures a guided swivel movement even in the event of lateral tilting of the maxillary part 2. Each of the spherical heads 9 is provided with a central working surface 10 for engagement with the tips of a transfer facility for the assembly of a mandibular model on the model block 6 in proper relation to the articulation.

The base plate 4 of mandibular part 1 is generally T-shaped with the model block 6 being supported on an outwardly extending leg 11 and the columns 5 extending from an arm which is oriented transversely with respect to leg 11. The mandibular part 1 is essentially in the form of a stand which is provided with feet 13, 14 and 15 of adjustable height. The model block 6 forms the secondary block of a known "Quicksplit-Magnetofix" system which has, on the surface which engages a primary block, individual raised areas 16 which can be brought in to engagement with notches in the bottom surface of the primary block.

The maxillary part 2, as may best be seen from FIG. 1, comprises a guide block 18. A base plate 17 is supported from and projects outwardly from guide block 18. Guide block 18 is arranged between a pair of independently adjustable outer arms 19, 20. The guide block 18 and the arms 19, 20 form a support section which is mounted on the hinge axis 3 via guide members 21. Guide members 21 are preferably spherical, half-shells mounted on the arms 19, 20 for engagement by the spherical heads 9. The ball and socket type joints defined by the guide members and spherical heads thus permit the outer arms 19, 20 to simulate the articular cavities of the maxilla. In order to transfer the swivel movement of the arms 19, 20 to the base plate 17, the arms 19, 20 engage opposite sides of the guide block 18 in the manner to be described below. The outer arms 19, 20 are arranged on either side of the center line 100 of the base plate 17 and guide block 18, i.e., the maxillary center line, and on either side of the longitudinal line 200 of the base plate 17 and guide block 18, as a right arm 19 and a left arm 20. The arms 19, 20 and guide block 18 are spatially displaceable relative to one another, it being possible for the arms 19, 20 to be adjusted independently of one another relative to the guide block 18 in the manner to be described below. This spatial displacement is preferably effected in two mutually perpendicular directions, i.e., vertically in direction C (parallel to longitudinal line 200) and horizontally in direction D (parallel to the center line 100). A unilateral or asymmetrical displacement of the arms 19, 20 relative to the guide block 18 results in a displacement of the maxillary model with a lateral and/or vertical shift relative to the articulated axis 3, as described in further detail below.

As noted above, the bearing points of the maxillary part 2 on the mandibular part 1 comprise the joints defined by the spherical half-shells 21 which form seats for the spherical heads 9. In order to prevent the parts 1 and 2 from becoming detached, safety means, indicated schematically at 22, are provided. As may be seen from FIG. 3, the socket defining guide members 21 are arranged in attachment members 23 so as to allow the adjustment in the spacing between the columns 5. Each attachment member 23 is held on its respective arm by means of a locking screw 24 and is displaceable along a slot 25 in the direction indicated by the double arrows B on FIG. 3.

Figure 3:
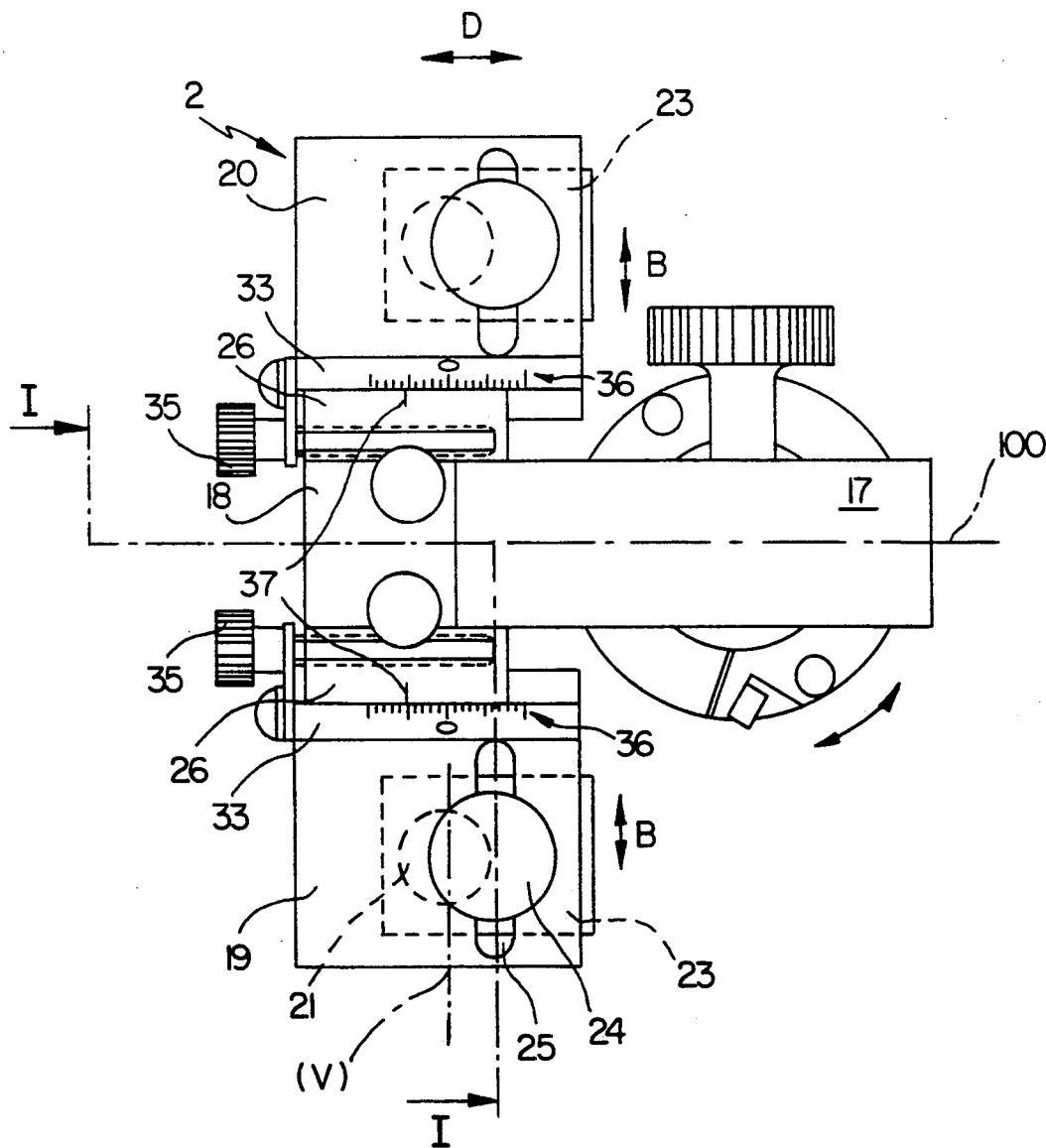
FIG. 3 is a top plan view of the maxillary support of the apparatus of FIG. 1.

As also shown in FIG. 3, the outer arms 19, 20 are designed with mirror-image symmetry with respect to the center line 100 and are respectively laterally connected to the guide block 18 via sliding bodies 26. The sliding bodies 26 are also designed with mirror-image symmetry with respect to the center line 100. The construction of the sliding bodies 26 and the interconnection thereof to the guide block 18 and the outer arms 19, 20 can be seen from FIG. 4 viewed in conjunction with FIG. 1.

Figure 4:
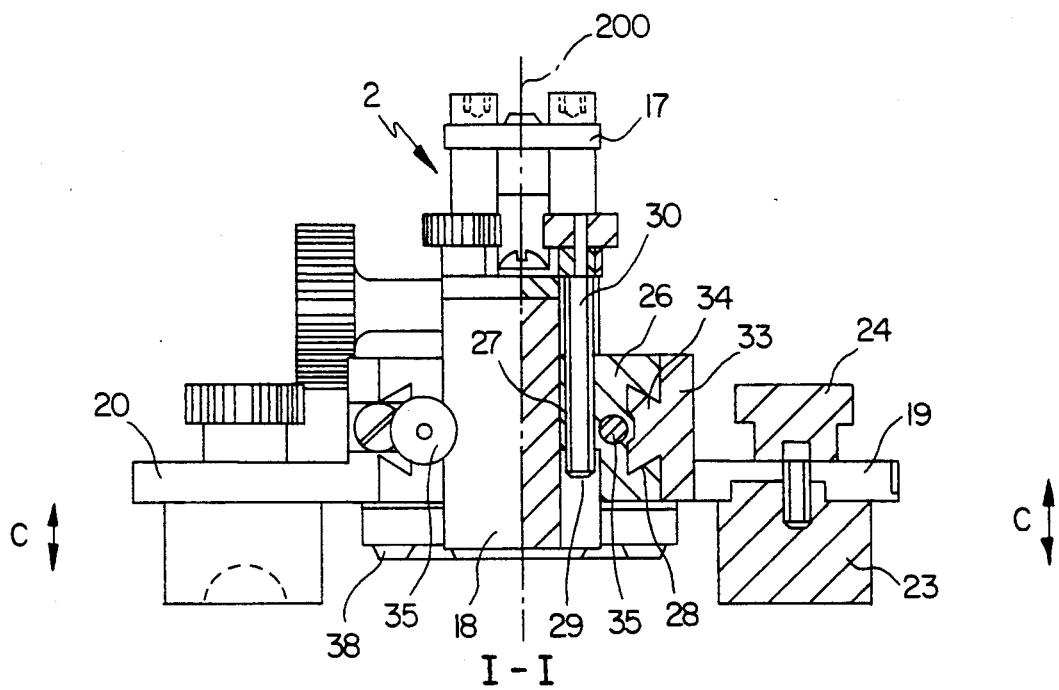
FIG. 4 is a partial cross-sectional view of the maxillary support of FIG. 3, the view of FIG. 4 being taken along line I—I of FIG. 3.
Figure 5:
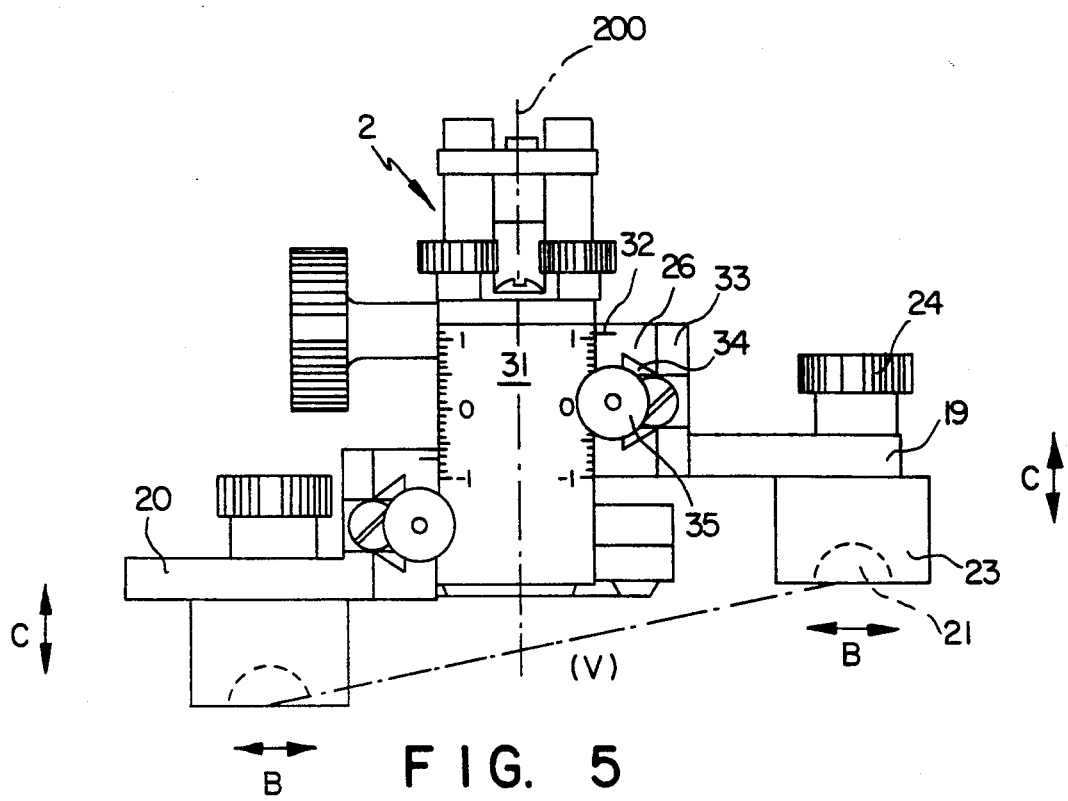
FIG. 5 is a rear view of the maxillary support of FIG. 3, FIG. 5 demonstrating an asymmetrical positioning of the outer arms of the maxillary support.

The sliding bodies 26 are essentially parallelpiped structures which are provided with an attachment 27 on a first side. The attachment 27 defines a first guide path 29. The sliding bodies 26 are also provided, on a second side disposed oppositely from attachment 27, with a dovetail slot 28 which defines a second guide path. These guide paths lie in substantially perpendicular planes. The guide block 18 has, on the sides which face the outer arms 19, 20, means 29 which defines a further guide path extending parallel to the longitudinal axis 200 in direction C. The guide path defining means 29 receives the guide path defining attachment 27 of the sliding body 26 as shown in FIG. 4. An adjustment screw 30 is provided for shifting the sliding body 26 along the guide path 29. Screw 30 is rotatably captured in the guide block 18 and extends along the guide path 29. The attachment 27 is provided with a thread which is engaged by the screw 30. Accordingly, a defined longitudinal shift of a sliding body 26 in the direction indicated by the double arrows C on FIG. 4 is possible by turning screw 30. The outer arms 19, 20 can thus be displaced independently of one another by shifting individual of the sliding bodies 26, in a direction which is parallel to the longitudinal line 200 and consequently is also preferably parallel to the orientation of the base plate 17. The guide body 18 has, as may be seen from FIG. 5, a pair of aligned scales 31 on its rear face. These scales enable the spatial displacement of the outer arms 19, 20 to be individually noted and recorded. The scales 31 are located along the outer edges of the side 31 of guide block 18 so as to be juxtapositioned to the sliding bodies 26. The sliding bodies 26 each carry a graduation mark 32 which cooperates with the scales. A differential shift of the two sliding bodies 26 in the direction C results in asymmetric positioning of the sliding bodies 26, and thus of the outer arms 19, 20, relative to the longitudinal line 200, i.e., the imaginary connecting line (V) of the outer arms 19, 20 forms an angle with the longitudinal line 200 which is other than 90° as indicated on FIG. 5.

The outer arms 19 and 20 are slidably mounted in respective of the sliding bodies 26. These slidable connections are established by providing each of the outer arms with a flange-like connection piece 33 having a dovetail shaped extension 34 which is received in the guide path defining slot 28. Accordingly, the arms 19, 20 may be displaced relative to the associated sliding body 26 and thus relative to the guide block 18. An adjustment screw 35 is provided for controlling the displacement of each outer arm relative to the guide block. As may best be seen from FIG. 3, the adjustment screws 35 are held stationary on the connection pieces 33 and extend into a threaded bore provided in the associated sliding body 26, these threaded bores extending parallel to the guide paths defined by the slots 28. Thus, by turning the adjustment screws 35, the sliding bodies may be shifted relative to each other in the direction indicated in FIG. 3 by the double arrow D. The displacement between the outer arms 19, 20 may, accordingly, be selected. The flange-like connection pieces 33 are each provided with a scale 26 on the top side thereof. The sliding bodies 26 are each provided with a graduation mark which cooperates with a scale 36. Accordingly, the relative displacement between the sliding bodies, and thus between the outer arms, in direction D may be easily determined. As will be obvious to those skilled in the art, the graduation marks 37 on the sliding bodies 26 are aligned and thus a deviation from a symmetrical alignment of the outer arms 19, 20 will be readily apparent. A differential shift of the outer arms 19, 20 in direction D results in an asymmetric positioning of these arms relative to the center line 100, i.e., the imaginary connecting line V is skewed so that it is not transverse to the center line 100.

The base plate 17, which as noted above extends from the guide block 18, is designed as a support for an anatomically correct maxillary model. Thus, referring again to FIG. 1, a model block 38 is arranged on the base plate 17 in such a manner as to be movable in inclination, specifically in a plane perpendicular to the base plate. The model block 38 can be stopped at a selected inclination relative to the base plate 17 by means of a locking screw 40. The model block 38 forms the secondary block of a "Quicksplit-Magnetofix" system which has, on the surface thereof which engages the primary block, individual raised areas 41 which can be brought into clearance-free engagement with notches which are provided in the bottom surface of the primary block.

The operation of the above-described embodiment of the invention, for the purpose of determining the correct position of the mandible and for performing an occlusion analysis, will now be described. In employing the invention, the maxillary support 2 is first placed on the mandibular support 1 and the outer arms 19, 20 are positioned and locked on the hinge axis 3. The outer arms 19, 20 will thus define the bearing points of the maxillary support 2 on the axis 3. A subsequent sliding movement, in direction D, will have the following effect on the displacement of the maxillary model. A bilateral, identical actuation of the adjustment screws 35 produces a purely dorsal or ventral displacement of the guide body 18 relative to the outer arms 19, 20. As noted above, the base plate 17 which supports the maxillary model will be displaced with the guide body 18. The imaginary connecting line V between the outer arms 19, 20, or the bearing points of the outer arms 19, 20 on axis 3, with pure dorsal or ventral displacement, will be oriented transversely to the center line 100. A unilateral rotation of one of the adjustment screws 35, or a non-identical actuation of adjustment screws 35, will produce an asymmetric displacement of the outer arms 19, 20 on the guide body 18. This will result in the imaginary connecting line V intersecting the center line 100 at an angle which is smaller than or greater than 90°. Since the arms 19, 20 remain on the axis 3, the asymmetric displacement of the arms results in a translational displacement of the base plate 17 combined with a lateral deviation. Transposed to the human dentition, the outer arms 19, 20 simulate the articular cavities of the cranium. The displacement of these cavities relative to the hinge axis of the mandible can be derived from the position of the outer arms 19, 20 relative to the guide body 18 and, consequently, from the angle of the connecting line V relative to the center line 100. The relative displacement of the articular cavities can be transferred to the movement of the condyles, so that the displacement of the condyles can be determined from the displacement of the articular cavities which is determined. The degree of asymmetry can be read by viewing the scales 36 and associated graduation marks 37.

The sliding movement in direction C (FIGS. 4 and 5) has a corresponding effect on the displacement of the maxillary model. That is, a caudal or cranial shift of the guide body 18 relative to the outer arms 19, 20 may be produced. By comparing FIGS. 4 and 5, it may be seen that the outer arms 19, 20 may be symmetrically or asymmetrically positioned relative to one another. The degree of asymmetry can be read from scale 31 employing the graduation marks 32.

A method for determination of the jaw relation of a patient in accordance with the present invention may comprise the following steps. Firstly, models of the maxilla and mandible of a patient are prepared and are mounted on the primary blocks of a control block system. These models are fixed in plaster independently of one another and are thus anatomically correct. The maxillary model is preferably fixed in plaster with reference to the cranium and the mandibular model is preferably fixed with reference to the patient's hinge axis. For the purpose of fixing the maxillary model in plaster with reference to the cranium, the row of teeth of the maxilla can be set parallel to the bipupillar line of the patient. The mandibular model is secured on the secondary block 6 of the mandibular part 1 of the above-described apparatus. The maxillary model is placed on the fixed mandibular model in an instantaneous occlusal position, preferably the central occlusion position. In order to achieve a connection of the maxillary model to the maxillary support 2 in this central occlusion position, the position of the secondary block 38 is altered by means of producing three-dimensional movement thereof until the secondary block 38 of the maxillary support 2 fits, in a clearance-free manner, into the primary block of the maxillary model in the ICP. Since the secondary block 38 is secured on the guide body 18 and the outer arms 19, 20 via the base plate 17, the requisite change in position of the secondary block 38 is achieved by means of an individual displacement of the outer arms 19, 20 in the vertical direction C, the horizontal direction D and, where appropriate, in the sagittal direction B.

The positioning of the arms 19, 20 described above, i.e., the adjustment of these arms such that the secondary block 38 engages the maxillary model in its instantaneous occlusal position, will make any asymmetric displacement of the maxillary part identifiable via the values which can be read from the scales 31, 33. Thus, the malpositioning of the mandible can be established from the instrumentally adjustable position of the maxillary model. Different values for the arms 19, 20 in directions C and D indicate that the mandible is displaced in the central occlusion position with a vertical and/or horizontal shift. This jaw relationship present in the patient in the central occlusion position is referred to as the actual position.

The physiological jaw relation, and thus the intended position, can be achieved by means of displacement of the maxillary model starting from the actual position. The intended position is obtained by symmetrical alignment of the outer arms 19, 20 on the maxillary support 2 and superpositioning of the maxillary center line and the mandibular center line. For this purpose, starting from the values read from the scales 31, 33, the positions of the outer arms 19, 20 are altered by actuation of the adjustment screws 30 and 35 until a symmetrical positioning of the outer arms relative to the lines 100 and 200 is achieved. The outer arms 19, 20 can thereafter be aligned by means of adjustment screw 24 so as to bring the maxillary center line and the mandibular center line from a parallel position into the superimposed position. The resulting jaw relation for the intended position indicates the therapeutic mandibular position and the malocclusions which are responsible for the non-physiological jaw relation.

While the invention has been described in connection with what is presently considered to be the most practical and preferred embodiment, it is to be understood that the invention is not limited to the disclosed embodiment, but rather is intended to cover various modifications and equivalents included within the spirit and scope of the appended claims.

What is claimed is:

1. A method of occlusion analysis wherein a maxillary model and mandibular model from a patient are fixed in plaster independently of one another and anatomically correctly, said method comprising the steps of placing the models one upon the other in an instantaneous occlusal position, determining the positioning of the articular cavities of the maxillary model relative to the hinge axis of the mandibular model with the models in the instantaneous occlusal position, displacing the maxillary model relative to the mandibular model to produce symmetrical alignment of the articular cavities relative to the hinge axis, and determining the resulting jaw relationships in order to analyze the malocclusions.

2. The method of claim 1 wherein the maxillary model and mandibular model are placed one upon the other in the central occlusion position.

3. The method of claim 1 wherein the articular cavities and the hinge axis are simulated instrumentally on two support parts which can be swivelled relative to one another and on which the models are secured.

4. The method of claim 1 wherein the maxillary model is displaced relative to the mandibular model by means of displacement of articular cavities which can be moved independently of one another in a three-dimensional manner.

5. The method of claim 1 wherein the maxillary model is fixed in plaster with reference to the cranium and the mandibular model is fixed in plaster with reference to the hinge axis.

6. The method of claim 5 wherein, for fixing the maxillary model in plaster with reference to the cranium, the row of teeth of the maxilla is set parallel to the bipupillar line of the patient.

7. Apparatus for use in the determination of the relationships between the jaws of a patient comprising a mandibular part and a maxillary part, each of said parts having base plate means for supporting a jaw model, means for supporting said maxillary part from said mandibular part, said supporting means defining a hinge axis for said maxillary part, said maxillary part having a pair of outer arms and a guide body, said arms being respectively disposed at a pair of opposite sides of said guide body, said maxillary part base plate means being supported from said guide body, said maxillary part further having support means for said outer arms, said outer arm support means permitting independent displacement of said outer arms relative to said guide body, said outer arm support mans each including a sliding body, said sliding bodies being coupled to said guide body so as to be slidably displaceable relative thereto, each of said arms being coupled to its associated sliding body so as to be slidably displaceable relative thereto.

8. The apparatus of claim 7 wherein the sliding bodies each include a first guide attachment defining a first guide path and means defining a second guide path, said guide paths cooperating respectively with a first guide path in the opposite side of the guide body and with second guide attachments on the associated outer arm.

9. The apparatus of claim 8 wherein the longitudinal extents of the first guide attachment and of the second guide path run perpendicular to each other.

10. The apparatus of claim 7 wherein the outer arms and the sliding bodies are designed in mirror image relative to the longitudinal axis of the guide body.

11. The apparatus of claim 7 wherein said support means for said outer arms further comprise means on said arms which form seats and means on said means for supporting said maxillary part from said mandibular part which define joints which cooperate with said seats, said seats and joint defining means defining said hinge axis and simulating an articulated human jaw hinge axle.

12. The apparatus of claim 11 wherein said seat defining means are arranged in attachments which are securable on the outer arms so as to be laterally displaceable relative to a center line of the baseplate means and the longitudinal line of the guide body.

13. The apparatus of claim 7 further comprising scale means for permitting determination of the independent displacement of said two outer arms relative to said guide body, said scale defining means including a co-displaced graduation mark which is a measure of the displacement.

14. The apparatus of claim 7 wherein the jaw models are each secured via a control block on the mandibular part or maxillary part.

15. The apparatus of claim 14 wherein the control block for the maxillary model is held on the maxillary part so as to be movable in inclination.

* * * * *